United States Patent [19]

Kramer

[11] Patent Number: 4,891,966
[45] Date of Patent: Jan. 9, 1990

[54] PROCESS AND APPARATUS FOR MEASUREMENT OF VOLATILE RESIDUALS

[75] Inventor: Anatoly I. Kramer, Winston-Salem, N.C.

[73] Assignee: R. J. Reynolds Tobacco Company, Winston-Salem, N.C.

[21] Appl. No.: 363,361

[22] Filed: Jun. 5, 1989

Related U.S. Application Data

[63] Continuation of Ser. No. 291,710, Dec. 29, 1988, abandoned.

[51] Int. Cl.⁴ ............................................. G01N 7/14
[52] U.S. Cl. ...................................... 73/19; 366/307
[58] Field of Search ................... 73/19; 366/325, 327, 366/329, 330, 307

[56] References Cited

U.S. PATENT DOCUMENTS

| | | | |
|---|---|---|---|
| 1,722,115 | 7/1929 | Sonsthagen et al. | 241/97 |
| 2,246,054 | 6/1941 | Marty | 241/97 |
| 2,711,644 | 6/1955 | Myers | 73/19 |
| 2,771,111 | 11/1956 | Seyfried | 241/292.1 |
| 2,788,038 | 4/1957 | Corcoran | 241/292.1 |
| 2,796,006 | 6/1957 | Chaplin | 241/34 |
| 2,918,956 | 12/1959 | Otto | 241/97 |
| 4,469,444 | 9/1984 | Gmeiner et al. | 366/144 |

Primary Examiner—John Chapman
Assistant Examiner—Joseph W. Roskos
Attorney, Agent, or Firm—Grover M. Myers

[57] ABSTRACT

A process and apparatus for measuring volatile residuals in a material utilizes high speed cutting and circulating blades in a closed container. The cutting blades reduce the size of the particles and thereby expose greater amounts of particle surface area. The circulating blades continually direct particles of material into contact with the cutting blades and also uniformly distribute the volatile residuals throughout the closed container.

23 Claims, 2 Drawing Sheets

PROCESS AND APPARATUS FOR MEASUREMENT OF VOLATILE RESIDUALS

This is a continuation of co-pending application Ser. No. 291,710, filed on Dec. 29, 1988, now abandoned.

FIELD OF THE INVENTION

The present invention is directed generally to a process and apparatus for the rapid measurement of a volatile residual in a solid material. More particularly, the present invention is directed to a process and apparatus for liberation and measurement of a residual gas volatile solvent, or the like from a solid material. In one preferred aspect, the present invention provides a process and apparatus for liberation and measurement of residual gas in treated tobacco particles.

BACKGROUND OF THE INVENTION

It is generally known in the art to treat tobacco particles to various expansion processes. These often involve subjecting the tobacco to contact with various treating gases, such as propane, ethane, carbon dioxide or chlorofluorocarbons under high pressure conditions. These treating gases typically do not chemically bind themselves with the tobacco during treatment. However, they do become absorbed into the many cavities which are found in the expanded tobacco particles. These treating gases may be held in the cavities of the tobacco particles for a significant period of time and will slowly diffuse into the atmosphere at, for example, a tobacco storage facility. Similarly, solid foods such as, for example, coffee, are often treated with volatile solvents for extracting materials such as caffeine, for adding flavors, and the like. Often, the treated food will contain trace amounts of such solvents or treating agents. Likewise, plastic films, fibers, and particles often include trace amounts of residual solvents or other volatile materials.

In all of the above cases, it is desirable to rapidly and accurately determine the amount of the residual materials retained by the solid. For example, when the treating gas is propane or another hydrocarbon, in the case of tobacco, the amount of residual gas or volatile liquid left in the treated tobacco particles is preferably accurately determined so that the potential amount of a flammable gas which may be released by the treated tobacco particles can be correctly ascertained. In the case of foods and plastics, accurate determination of residuals is important for minimization of undesirable materials which might contaminate taste or smell, or which may otherwise be undesirable. Additionally, information regarding the amount of volatile residuals held by the treated solid, e.g., tobacco, is also important for control of the treatment process.

The generally known head space analytical technique for determining the amount of residuals, such as propane in treated tobacco, requires up to 3 days to perform. This technique is dependent on the equilibration of the residual gas with the surrounding atmosphere and relies on natural molecular diffusion of the residual gas or volatile material out of particles, such as tobacco, and into the surrounding atmosphere. The primary driving force toward this equilibration is the gas concentration gradient between the treated particles and the surrounding atmosphere. Thus attempts to shorten the time period, such as by heating a tobacco sample, have not been effective to significantly reduce the time required for the equilibrium point to be reached.

It is clear that an analytical technique to evaluate gas or other volatile residuals, which takes up to 3 days to perform is not satisfactory. Thus there clearly exists a need for a process and apparatus for the measurement of volatile residuals. The process and apparatus for measurement of volatile residuals, as will be discussed subsequently, provides a solution to this problem and is clearly an advance in the art.

SUMMARY OF THE INVENTION

It is an object of the present invention to provide a rapid process and apparatus for measurement of volatile or gas residuals in a solid.

Another object of the present invention is to provide a process and apparatus for measurement of gas or other volatile residuals in tobacco particles, food particles or plastic fibers, films or particles.

A further object of the present invention is to provide an apparatus for quickly liberating residual volatile materials and uniformly distributing the liberated residual material within a closed chamber.

Still a further object of the present invention is to provide a process and apparatus for facilitating residual gas release through heating.

Even yet another object of the present invention is to provide a process and apparatus for measurement of gas residuals which can be accomplished in a short period of time.

As will be discussed in detail in the description of the preferred embodiment which is set forth subsequently, the process and apparatus for measurement of gas residuals in accordance with the present invention utilizes a hermetically sealable container having a means for reducing the size of a solid material, such as one or more rotatable cutting blades, and at least one recirculation means such as a separate circulating propellor blade to thereby repeatedly reduce the size of solids which contain non-chemically bonded gas or volatile liquid residuals within the sealed container and concomitantly to liberate this residual gas or volatile liquid in gaseous form. For example, expanded tobacco particles, which have typically been subjected to a high pressure expansion process, are placed in the closed container of the present invention where they are subjected to agitation and breaking or tearing of the cellular structure of the tobacco particles. This cutting or breaking of each particle into smaller particles increases exposed surface area and exposes the many cavities, contained within the particles, to the surrounding atmosphere. The residual gas, which was being carried in these cavities, is released to the closed atmosphere in the interior of the container. Uniform residual gas distribution in the container and circulation of the tobacco particles through the one or more cutting blades is facilitated by the circulating propellor blade assembly. After the apparatus has been operated for a suitable period of time, a sample of the atmosphere within the closed container can be withdrawn and analyzed, such as by gas chromatography. By comparing initial and final residual material content readings, the total amount of liberated material can be calculated based on the known closed container volume. The residual material content can then be determined based on the known weight or volume of the sample, e.g., tobacco.

The process and apparatus for measurement of volatile residuals in accordance with the present invention utilizes the positive step of subjecting the particles of tobacco or the like to be analyzed to both cutting or breaking and agitation. In contrast with prior passive procedures, the process and apparatus of the present invention actively reduces the size of the solid material to greatly increase the surface area and number of cavities in the particles which are exposed to the atmosphere within the closed container. This significantly increases the rate of release of the residual gas.

The process and apparatus for measurement of volatile residuals in accordance with the present invention allows a residual gas analysis of a sample in a period of less than 30 minutes, and as short as 3 minutes or less in the case of tobacco. This is in marked contrast to the long periods required by prior analytical techniques. As will be readily appreciated, this substantially shortened length of time allows the analysis of residual volatile content of treated tobacco particles to maintain pace with treatment processes such as faster high pressure tobacco expansion processes. Analysis of the product's residual content will thus not lag behind production of the product itself.

The process and apparatus for measurement of gas residuals utilizes both size reduction and recirculation means, e.g., cutting and circulating blades, in a saled container to reduce particle size and to thereby expose more of the cavities and surface area of the solids to the atmosphere. The residual volatile content is thus more quickly and effectively released into the closed chamber and is uniformly mixed therein. A sample of this mixture may then be removed for analysis. It will thus be understood that the process and apparatus in accordance with the present invention represents a significant advance in the art.

BRIEF DESCRIPTION OF THE DRAWINGS

While the novel features of the process and apparatus for measurement of volatile residuals in accordance with the present invention are set forth fully and completely in the appended claims, a full and complete understanding of the invention may be had by referring to the detailed description of the preferred embodiment which is set forth subsequently, and as illustrated in the accompanying drawings, in which:

DESCRIPTION OF THE PREFERRED EMBODIMENT

Figure 1:
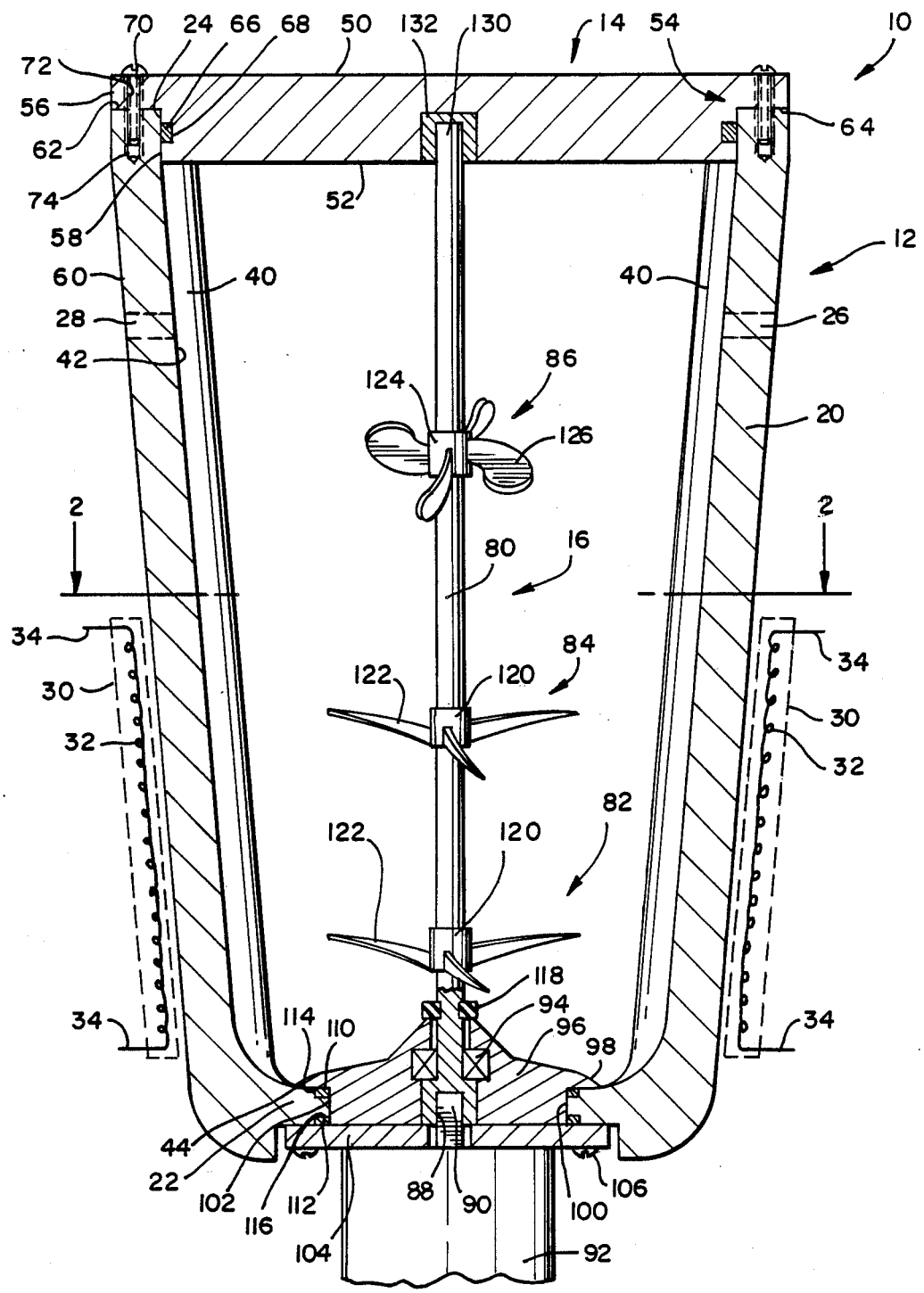
FIG. 1 is a side elevation view, partly in cross-section of the apparatus for measurement of volatile residuals in accordance with the present invention.

Referring initially to FIG. 1 there may be seen generally at 10 an apparatus for measurement of volatile residuals in accordance with the present invention. Apparatus 10 includes a container 12, a closure assembly 14 for container 12, and a circulating and cutting blade assembly, generally at 16 carried within the container 12. As will be discussed in more detail shortly, particles of material, such as tobacco, which have absorbed residual gas, are placed in container 12 which is then sealed with closure 14. The cutting blade and circulating assembly 16 is caused to turn at a relatively high rate of speed. The particles of material are thus reduced in size so that the absorbed residual volatiles may be released in gaseous form. This released gas is evenly distributed within closed container 12 and may then have a representative sample withdrawn for analysis In this way the residual content in a sample may be quickly and accurately ascertained.

Returning to FIG. 1, container 12 is generally frusto-conical in shape. A side wall 20 is inclined inwardly at a small angle, such as 5°–15° from vertical. A bottom 22 of container 12 slopes, or is curved toward the center thereof. The container also includes an open mouth 24. In the preferred embodiment, container 12 is made of a suitable metal, such as aluminum and is generally similar in overall size to a typical home or commercial blender. A suitable check seal 26 is schematically depicted in the side wall 20 of container 12 as is a suitable gas sampling port 28. In actual usage this gas sampling port 28 may be connected to an analytical assembly such as a gas chromatography device. If desired, an optional heating jacket 30, which may carry suitable electric resistance heating wires 32, may be removable placeable about the walls 20 of container 12. This heating jacket will be understood as being connectable to a suitable controllable power source (not shown) through leads 34.

A plurality of turbulence increasing ribs 40 are either formed integrally with, or attached to an inner surface 42 of the sidewall 20 of container 12. These ribs 40 are typically generally equally spaced about inner surface 42 and extend generally vertically upwardly from an inner surface 44 of container bottom 22 and terminate generally adjacent mouth 24 of the container 12. These ribs 40 are depicted as being generally semi-circular in cross section, as seen in FIG. 2 but may have other shapes which will impart turbulence to the circulating material within container 12 without trapping any material.

Container closure 14, as seen in FIG. 1, is generally disk-shaped and is sized to cooperatively interfit with the open mouth 24 of container 12. A top surface 50 of closure 14 is generally planar, as is a bottom surface 52. These surfaces are separated by a stepped side wall 54 which has a larger diameter upper side surface portion 56 and a reduced diameter lower side surface 58. As may be seen in FIG. 1, upper side surface 56 is generally aligned with an outer surface 60 of sidewall 20 of container 12 while lower side surface 58 of closure 14 is complimentary in diameter with the inner wall 42 of container 12. A generally horizontal flange 62 extends between upper and lower side surfaces 56 and 58, respectively of closure 14. This flange 62 abuts an upper rim 64 of open mouth 24 of container 12. A suitable sealing O-ring 66 is carried in a circumferential groove 68 on lower side surface 58 of closure 14. Suitable securement means, such as screws 70 which pass through apertures 72 in closure 14 and which are receivable in threaded bores 74 in the upper rim 64 of container 12, are provided to releasably secure closure 14 to container 12. It will be understood that this closure 14 is sealingly securable to container 12 through O-ring 66 and securement means 70 to insure that no gas can enter or escape from container 12 when closure 14 is in place.

Figure 2:
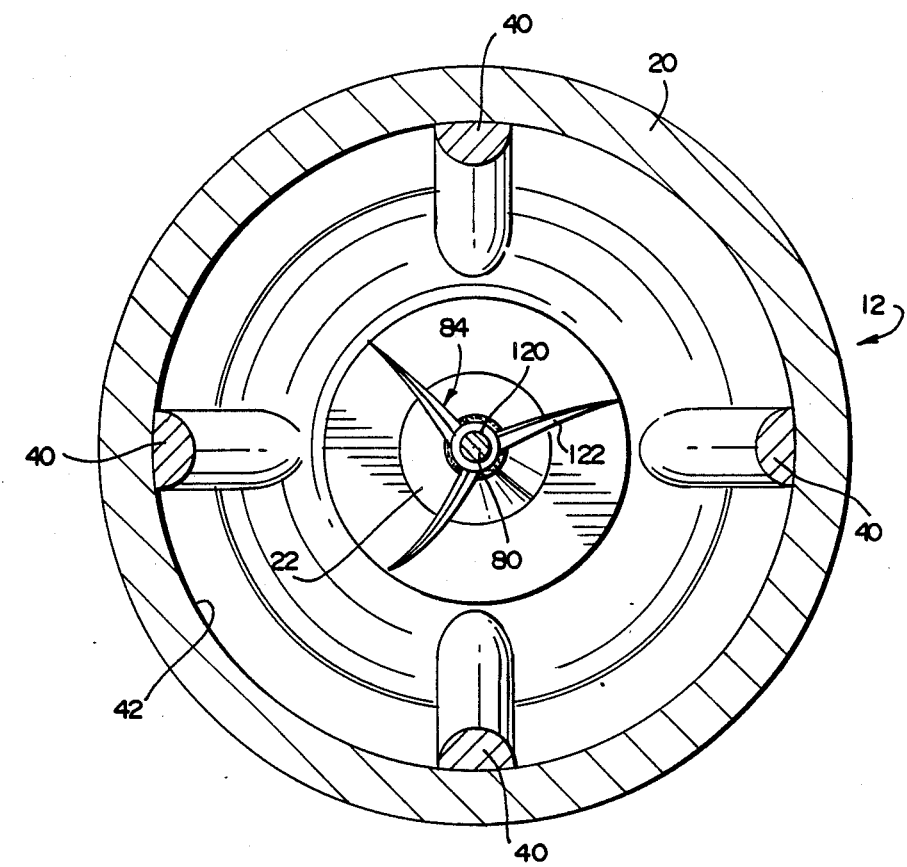
FIG. 2 is a cross-sectional view of the invention taken along line 2—2 of FIG. 1.

A central rotatable shaft 80 carries preferably spaced first and second cutting blades 82 and 84 and a circulating propellor 86, all as may be seen in FIGS. 1 and 2. Spacing between blades 82 and 84 is not critical but is generally sufficient so that tobacco is not trapped between the blades. Similarly, the location of propellor 86 is not critical so long as sufficient space is provided to ensure recirculation of the solids in the container. At its lower end, shaft 80 has a socket 88 which will receive a stub shaft 90 of a suitable high speed drive motor 92. A generally conventional bearing assembly 94 is positioned in a hub 96 and supports shaft 80 for rotation. Hub 96 is provided with an upper lip 98 which engages inner surface 44 of container bottom 22, and a central barrel 100 which engages a central opening 102 in container bottom 22. A lower sealing plate 104 is attached to container bottom 22 by suitable screws 106 and has a central hole 108 which is aligned with socket 88 in rotatable shaft 80. Upper and lower sealing O-rings 110 and 112, respectively, are placed in cooperatively sized grooves 114 and 116 adjacent the central opening 102 in container bottom 22. These O-rings insure a leak proof seal between hub 96 and central opening 102. A seal 118 such as a V-ring seal (U.S. Pat. No. 3,713,659) is provided at the bottom of shaft 80 to ensure that there is no gas leakage around the shaft.

Spaced cutting blades 82 and 84 are essentially the same and each has a central sleeve 120 and several radially extending cutting blades 122. While at least a first cutting blade 82 must be provided, two are preferred. Circulating propellor 86 also has a central propellor sleeve 124 and a plurality of radially extending propellor blades 126. As seen in FIG. 1, the cutting blades 82 and 84, and circulating propellor blade 86 are all removably attached by any suitable means to rotatable shaft 80 in a spaced array. The circulating blade 86 is positioned above the cutting blade or blades 82 and 84 and may have blade pitches which either pull material up through the cutting blades or alternatively direct it down through these blades 82 and 84. Thus circulating propellor blade 86 continually directs particles into the cutting blades. At the same time, it continually reexposes the particles to the atmosphere in the closed container 12 and remixes the atmosphere to provide a homogenous mixture in the container.

An upper end 130 of rotatable shaft 80 is receivable in a bushing 132 which is placed centrally in the lower surface 52 of container closure 14. This bushing thus supports the upper end of rotatable shaft 80 and stabilizes it during its rotation. Rotation of shaft 80 is, as was discussed previously, effected by insertion of stub shaft 90 into socket 88 and actuation of drive motor 92. The speed of this drive motor may be controlled by suitable means which are not specifically shown. It will be understood that the container 12 is readily separable from drive motor 92 and that additional container supporting means, such as support legs could be provided, if desired.

It will be understood that other size reduction means can be substituted within the scope of the invention for cutting blades 82 and 84 or that other blade arrangements can be employed. For example, various milling or grinding arrangements can be employed as well as cutting blades of different shape arrangements or operation.

In operation, a measured volume, such as for example 150–200 ml. of expanded tobacco particles, which have been previously subjected to a high pressure tobacco expansion process, are placed in container 12. This is accomplished by removal of container closure 14 and subsequent securement of closure 14 after the particles are in the container. The initial atmosphere inside the now closed container may be sampled and analyzed by withdrawal of a small sample through gas sampling port 28. The drive motor 92 is then activated and causes the shaft 80 to rotate at a high rate of speed which may be in the range of 10,000–25,000 rpm, with about 20,000 rpm being preferred for tobacco. The dry and freely flowable tobacco particles are contacted by the cutting blades 122 and these blades cut or tear the tobacco particles to reduce their size and to expose the internal cavities which contain the residual treating gas. If desired, the heating jacket 30 may be activated prior to, and during rotation of the shaft 80. It is to be noted that typically, the frictional forces generated during the cutting and shearing action within the container will impart some heat to the material being treated as an inherent part of the size reduction step. The cutting blades 122 do an effective job of reducing the size of the tobacco particles and thereby greatly increasing the total exposed tobacco particle surface area. This increase in exposed surface area increases the number of tobacco particle cavities which are opened to the atmosphere and thus dramatically reduces the time necessary to free the residual gas from the tobacco particles.

As is typical with a cutting blade device of this type, the cutting blades 82 and 84 are not also effective particle circulators. Thus, the circulating propellor 86 is used to cause all of the dry and free flowing tobacco particles to contact the cutting blades 82 and 84. The propellor blades 126 are not intended to function as cutting blades and can be pitched to either pull particles up through the cutting blades 82 and 84 or alternatively to direct particles down into the cutting blades. These propellor blades 126 also circulate the residual gas liberated by the cutting blades and effect a uniform residual gas distribution within the total volume of the container. Additionally, the ribs 40 in the container are effective in increasing the turbulence in the container and thus in increasing particle contact with the cutting blades and uniform distribution of the residual gas.

Once the drive motor has been operated for a certain period of time, such as, for example, 1–2 minutes, the motor may be turned off. A sample of the atmosphere within the still closed container 12 may be withdrawn through the gas sample port 28 and subjected to analysis, such as by gas chromatography. A comparison of the initial and final analysis results, in conjunction with a knowledge of the volume of the closed container yields the amount of residual gas released from the tobacco particles. Since the initial volume or weight of the expanded tobacco particles is also known, a determination of the gas residual amount per unit volume or unit mass of tobacco particles can be readily calculated. This measurement of the residual gas or other volatile thus allows one to accurately determine the residual content in the tobacco and can be important for control of the treatment process.

In marked contrast to the prior measurement technique and process, which could require up to 3 days for the equilibration of the residual gas with the surrounding atmosphere as a result of molecular diffusion, the process and apparatus for measurement of gas residuals in accordance with the present invention requires an analysis time of generally less about 30 minutes, advantageous less than 10–15 minutes, and for tobacco, less than 3 minutes. Thus the process and apparatus of the present invention is a substantial advance in the art.

This process, while having been discussed with respect to the liberation of residual gas or other volatiles from tobacco particles is, as was discussed previously, equally useful for other materials. It will be recalled that the process and apparatus can also be used to analyze retained solvents or the like in plastics or retained materials in foods, such as decaffeinated coffee. Thus the process and apparatus is not limited solely to usage with tobacco.

While a preferred embodiment of a process and apparatus for measurement of gas residuals has been fully and completely set forth hereinabove, it will be apparent to one of skill in the art that a number of changes in the process and apparatus such as, for example, the particular residual gas being released, the size of the container, the number of cutting blades, the number of circulating blades, and the like could be made without departing from the true spirit and scope of the present invention which is accordingly to be limited only by the following claims.

What is claimed is

1. A process for measuring volatile residuals in a solid material, said process comprising:
   providing particles of said solid material having a volatile residual material retained within said particles,
   repeatedly reducing the size of said particles in a hermetically sealed chamber and liberating said volatile residual material as a gas within said chamber; and
   removing a sample of said gas from said hermetically sealed chamber and analyzing said sample and providing a measure of said gas residual.

2. The process of claim 1 further including reducing the size of said particles in said chamber by using at least a first rotating cutting blade.

3. The process of claim 2 including reducing the size of said particles by using first and second spaced rotating cutting blades.

4. The process of claim 2 further including recirculating said particles in said chamber to said at least first rotating cutting blade by using a circulating means.

5. The process of claim 4 including operating said cutting blade and said circulating means concurrently.

6. The process of claim 4 further including utilizing said circulating means for uniformly distributing said liberated volatile residuals throughout said chamber.

7. The process of claim 1 further including placing said particles in said chamber in a dry and free flowing state.

8. The process of claim 1 further including providing a plurality of turbulence increasing ribs in said chamber.

9. The process of claim 1 wherein the step of providing said particles includes providing particles of tobacco.

10. The process of claim 1 wherein the step of providing said particles includes providing particles of low density expanded tobacco.

11. The process of claim 1 including conducting said size reduction of said particles for a period of time less than 15 minutes.

12. The process of claim 1 including conducting said size reduction of said particles for a period of time less than 10 minutes.

13. The process of claim 1 including conducting said size reduction of said particles for a period of time less than 5 minutes.

14. An apparatus for liberating and measuring volatile residuals in a material having volatile residuals therein, said apparatus comprising:
   a closeable container;
   a removable closure for said closeable container;
   a rotatable shaft positioned within said container;
   at least a first cutting blade assembly secured to, and rotatable with said rotatable shaft;
   at least a first circulating propellor assembly secured to, and rotatable with said rotatable shaft; and
   drive means to rotate said rotatable shaft to cause said cutting blade assembly to contact said particles to sever said particles into smaller particles and further to cause said circulating propellor assembly to circulate said particles in said closed container.

15. The apparatus of claim 14 wherein said container is generally frustoconical and has a bottom, a sidewall and an open mouth.

16. The apparatus of claim 15 wherein said closure is positionable in said open mouth of said container.

17. The apparatus of claim 15 wherein said rotatable shaft is generally centrally positioned in said container.

18. The apparatus of claim 14 wherein there are first and second spaced cutting blade assemblies.

19. The apparatus of claim 14 wherein said circulating propellor assembly is secured to said rotatable shaft spaced from, and generally above said at least first cutting blade assembly.

20. The apparatus of claim 14 further including a heating jacket positionable in heat exchange relationship with said closeable container.

21. The apparatus of claim 17 wherein said rotatable shaft has an upper end which is receivable in a bushing in an under surface of said removable closure when said removable closure is placed on said closeable container.

22. The apparatus of claim 14 wherein said closeable container includes a plurality of turbulence increasing ribs within said closeable container.

23. The apparatus of claim 14 wherein said rotatable shaft is separably connectable to said drive means.

* * * * *